United States Patent
DeHeer et al.

(10) Patent No.: US 8,814,815 B2
(45) Date of Patent: Aug. 26, 2014

(54) ADJUSTABLE-SOLE, HINGED EQUINUS BRACE WITH TOE WEDGE

(76) Inventors: Patrick DeHeer, Carmel, IN (US); John H. Moorin, Carmel, IN (US); Ricky Heath, Fishers, IN (US)

(*) Notice: Subject to any disclaimer, the term of this patent is extended or adjusted under 35 U.S.C. 154(b) by 110 days.

(21) Appl. No.: 13/439,449

(22) Filed: Apr. 4, 2012

(65) Prior Publication Data

US 2012/0253253 A1 Oct. 4, 2012

Related U.S. Application Data

(60) Provisional application No. 61/471,302, filed on Apr. 4, 2011, provisional application No. 61/489,398, filed on May 24, 2011, provisional application No. 61/583,474, filed on Jan. 5, 2012.

(51) Int. Cl.
*A61F 5/00* (2006.01)

(52) U.S. Cl.
USPC .................. 602/16; 602/23; 602/26; 602/27

(58) Field of Classification Search
USPC ........................ 602/16, 23, 26–28; 128/882
See application file for complete search history.

(56) References Cited

U.S. PATENT DOCUMENTS

| | | | |
|---|---|---|---|
| 5,393 A | 12/1847 | Chamberlin | |
| 73,768 A | 1/1868 | Allen | |
| 265,942 A | 10/1882 | Burns | |
| 2,516,872 A * | 8/1950 | Hauser et al. | 602/27 |
| 2,827,897 A * | 3/1958 | Pawlowski | 602/16 |
| 2,943,622 A * | 7/1960 | Nelson | 602/16 |
| 3,958,567 A | 5/1976 | Callender, Jr. | |
| 4,632,096 A | 12/1986 | Harris | |
| 4,848,326 A * | 7/1989 | Lonardo | 602/26 |
| 4,981,132 A | 1/1991 | Chong | |
| 5,224,925 A * | 7/1993 | Varn | 602/28 |
| 5,490,831 A * | 2/1996 | Myers et al. | 602/26 |
| 6,024,713 A * | 2/2000 | Barney | 602/23 |
| 6,280,404 B1 | 8/2001 | Morinaka et al. | |
| 7,077,818 B2 | 7/2006 | Ingimundarson et al. | |
| 7,462,159 B1 * | 12/2008 | Shlomovitz et al. | 602/16 |
| 2004/0002672 A1 | 1/2004 | Carlson | |
| 2009/0069732 A1 | 3/2009 | Jackovitch | |
| 2010/0069807 A1 * | 3/2010 | Cox | 602/23 |

FOREIGN PATENT DOCUMENTS

DE 102008052369 10/2008
DE 102008052517 7/2010

OTHER PUBLICATIONS

J A Radford, et al., "Does stretching increase ankle dorsiflexion range of motion? A systematic review." Br J Sports Med, Aug. 22, 2006, pp. 870-875, 40.

* cited by examiner

*Primary Examiner* — Michael A. Brown
(74) *Attorney, Agent, or Firm* — D'Hue Law LLC; Cedric A. D'Hue

(57) ABSTRACT

Devices and processes used to treat ankle equinus. More specifically, the present disclosure relates to a brace and the corresponding method of use to treat equinus by stretching the Gastrocnemius muscle.

34 Claims, 4 Drawing Sheets

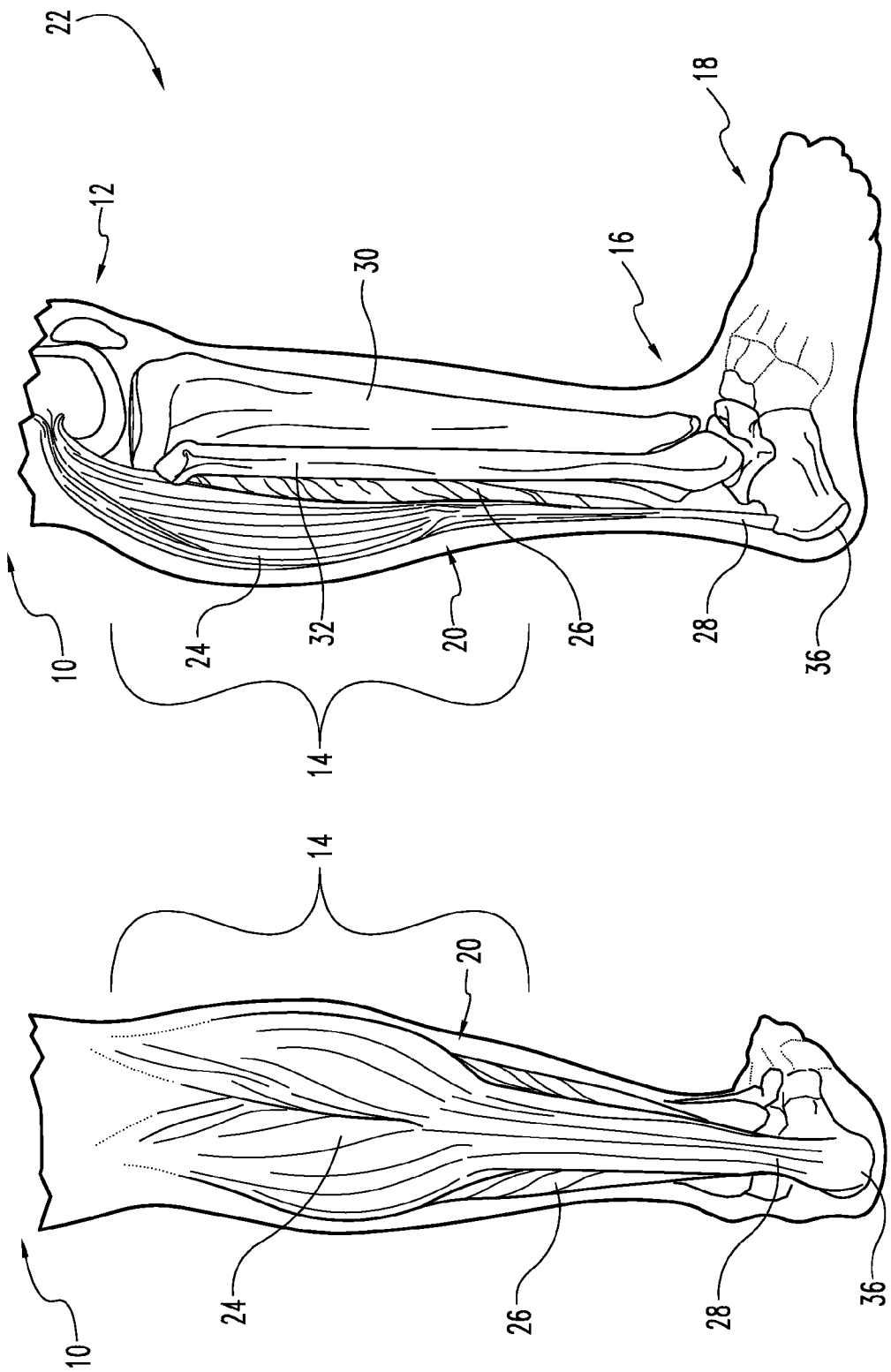

ADJUSTABLE-SOLE, HINGED EQUINUS BRACE WITH TOE WEDGE

REFERENCE TO RELATED APPLICATIONS

The present application claims priority from U.S. Provisional Patent Application Ser. No. 61/471,302, which was filed Apr. 4, 2011, under the title "EQ/IQ Equinus Brace"; U.S. Provisional Patent Application Ser. No. 61/489,398, which was filed May 24, 2011, under the title "Hinged Equinus Brace with Toe Wedge"; and U.S. Provisional Patent Application Ser. No. 61/583,474, which was filed Jan. 5, 2012, under the title "Adjustable-Sole, Hinged Equinus Brace with Toe Wedge," the disclosures of which are expressly incorporated by reference.

FIELD

The present disclosure relates to devices and processes used to treat ankle equinus. More specifically, the present disclosure relates to braces or device and their methods of use to treat equinus by stretching the Gastrocnemius muscle and/or the Soleus muscle.

BACKGROUND

Equinus is typically described as a condition in which the upward bending motion of the ankle is limited. Equinus is defined as the inability or lack of ankle joint dorsiflexion less than a right angle relative to the leg.

Equinus may result in a lack of flexibility past the right angle relative to the leg. Someone suffering with equinus may lack the flexibility to bring the top of foot 18 past a right angle (90°) relative to the leg and toward the front of the leg. A typical maximum ankle range of motion for dorsiflexion is indicated as twenty-five degrees (25°) less than a right angle relative to the leg. Equinus may also be characterized as a limited ankle range of motion for dorsiflexion which is no more than five (5°), ten (10°) or even fifteen degrees) (15°) less than a right angle relative to the leg.

There are several possible causes for limited range of ankle motion. Limited range of ankle motion is often due to tightness in the calf muscles (the soleus muscle and/or the gastrocnemius muscle). Shortening of the gastrocnemius muscle (also known as gastroc equinus) is a very common condition which may affect most people because the gastrocnemius muscle crosses two joints. The gastrocnemius muscle originates above knee 12 joint, while the soleus originates below knee 12 joint. Both muscles join to form the Achilles tendon, which attaches to the heel. Therefore, the gastrocnemius muscle crosses two joints: knee 12 and the ankle, while the soleus muscle only crosses the ankle joint.

Regardless of the cause of limited ankle motion, someone suffering with equinus can develop a wide range of foot problems. There are several ways to treat limited ankle range of motion, such as gastroc equinus, including stretching exercises, orthotics with heel lifts, padding, molded shoes, serial casting, as well as night splints and braces.

Many current night splints allow user 22 to sleep with their knees bent. Current night splints and braces do not lock knee 12 into extension as they do not extend above the knee. Failure to lock knee 12 into extension means that a person experiencing gastroc equinus does not stretch gastrocnemius muscle, and therefore is only stretching the soleus muscle.

Many current night splints and braces are awkward and uncomfortable for sleeping. Since night splints and many current braces are supposed to be worn throughout the night, an awkward or cumbersome night splint or brace may cause a user to either not get a good night's sleep or cause a user to remove the device. If user 22 does not get a good night's sleep, user 22 may not choose to use the device in the future. This lack of compliance leads to the current devices not performing their intended function.

Even if a knee is kept completely straight by a user, the night splint or brace is not the reason for a complete stretch of gastrocnemius muscle, because there is no above the knee extension locking the knee joint.

If the night splint or brace does not lock the knee in full extension while dorsiflexing the ankle joint, the device is not providing the preferred method of treatment.

BRIEF DESCRIPTION OF THE DRAWINGS

FIG. 1 is a back view of calf muscles with a knee at extension and an ankle at neutral position.

FIG. 2 is a side view of the calf muscles of FIG. 1.

DESCRIPTION

Figure 3:
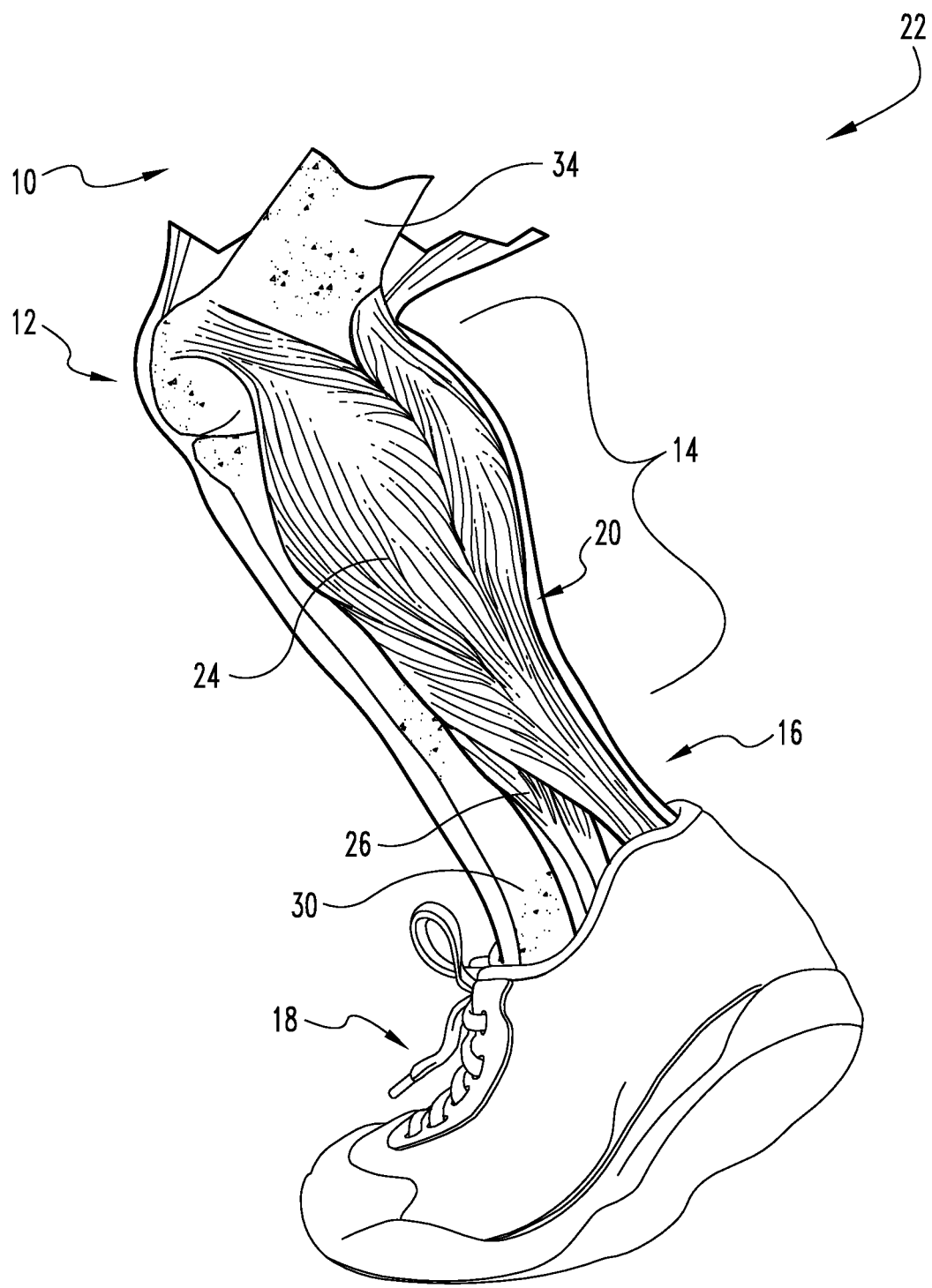
FIG. 3 is a perspective view of calf muscles with a knee in flexion and the ankle in dorsiflexion.

For the purpose of promoting an understanding of the principles of the invention, reference will now be made to certain embodiments illustrated in the disclosure, and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As shown in FIGS. 1 and 2, thigh 10, knee 12, calf 14, ankle 16, foot 18, and calf muscles 20 of user 22 are illustrated. Calf muscles 20 are shown as gastrocnemius muscle 24 and soleus muscle 26. Each of these muscles 24, 26 shares a common insertion (attachment) via Achilles tendon 28 into the posterior calcaneus. Soleus muscle 26 originates at the proximal to medial portions of tibia 30 and fibula 32. Soleus muscle 26 and gastrocnemius muscle 24 unite via their respective apponeurosis to form Achilles tendon 28. Unlike soleus muscle 26, gastrocnemius muscle 24 originates at posterior femur 34 just above knee 12 and also inserts into heel 36. Gastrocnemius muscle 24 crosses two joints: knee 12 and ankle 16.

As illustrated with knee 12 in extension and ankle 16 in normal position, soleus muscle 26 and gastrocnemius muscle 24 are not stretched to capacity in a person with normal ankle range of motion including maximum ankle dorsiflexion of twenty-five degrees (25°). In a person with limited ankle range of motion, such as equinus, soleus muscle 26 or gastrocnemius muscle 24 may be stretched to capacity with knee 12 in extension for gastroc equinus or gastrosoleal equinus and ankle 16 in normal position or in a dorsiflexed position.

As illustrated in FIG. 3, a person with limited ankle range of motion due to gastroc equinus, moving knee 12 from extension to flexion releases gastrocnemius muscle 24 from full stretch capacity. A person suffering from gastroc equinus may be able to place ankle 16 in dorsiflexion with knee 12 in flexion even though gastrocnemius muscle 24 is shortened.

Figure 4:
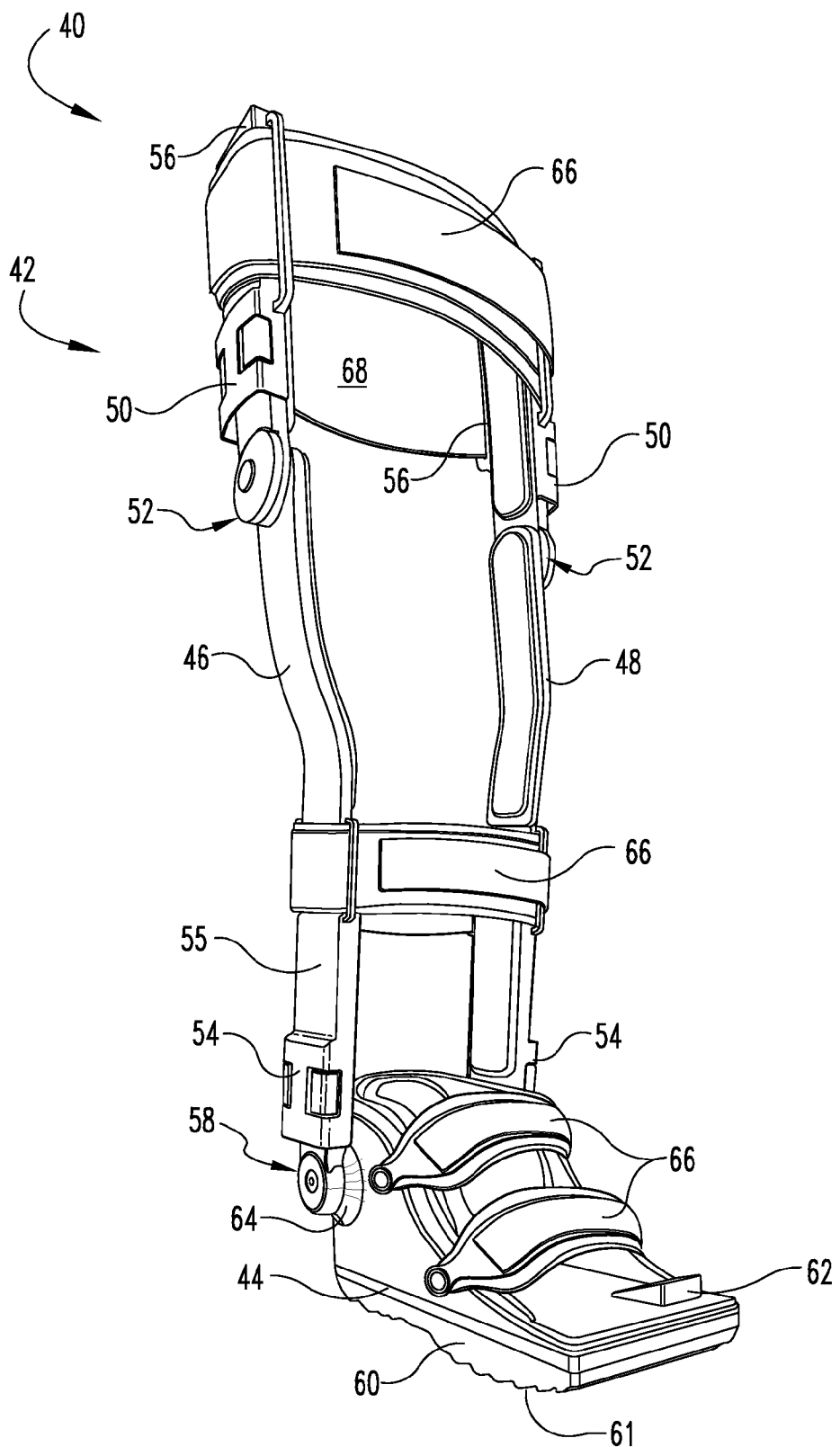
FIG. 4 is a perspective view of a brace/device according to an embodiment of the present disclosure.

Device 40 according to an embodiment of the present disclosure is illustrated in FIG. 4. Device 40 is constructed from plastic molded shell 42 including footplate 44, medial rod 46 and lateral rod 48. Medial rod 46 and lateral rod 48 are each terms used to describe a plurality of elongated rods 46, 48 and additional components. Medial rod 46 and lateral rod 48 each extend from above knee 12 of user 22 to foot 18 of user 22.

Medial rod 46 is described to correspond to the medial side of the leg of user 22. Lateral rod 48 is described to correspond to the lateral side of the leg of user 22. It is understood that in this embodiment each elongated rod can function as either medial rod 46 or lateral rod 48 depending upon the needs of user 22. It is envisioned that device 40 can be used on either leg of user 22. It is also envisioned that by switching device 40 from one leg of user 22 to the other leg of user 22, medial rod 46 becomes lateral rod 48 and vice versa.

Medial rod 46 and lateral rod 48 each include femur adjustment 50, knee hinge 52, and tibia adjustment 54. Femur adjustment 50 includes a slidably attached extension to femur rod 56 of either medial rod 46 or lateral rod 48. Femur adjustment 50 allows for proper sizing and fit of device 40 about the thigh of user 22. In one embodiment, femur adjustment 50 independently extends femur rod 56 to about the middle of thigh 10 of user 22. Femur adjustment 50 also facilitates use of device 40 with users of varying leg length.

Knee hinge 52 connects at least two of the plurality of elongated rods 46, 48. Knee hinge 52 is configured to be located somewhat at, below or above knee 12 of user 22.

Knee hinge 52 allows for anterior or posterior rotation of at least one of the plurality of elongated rods 46, 48. Rotation of femur rod 56 may aid in insertion of user's leg into device 40 or removal of user's leg from device 40. Knee hinge 52 also includes a locking feature which allows knee 12 of user 22 to be locked in extension. As discussed in greater detail below, locking knee in extension aids in stretching the gastrocnemius muscle of user 22. In the alternative, knee hinge 52 also allows for unlocking of knee 12 of user 22 in flexion. Unlocking knee 12 of user 22 in flexion may aid in isolated stretching of the soleus muscle of user 22.

Tibia adjustment 54 provides a slidably attached extension between tibial rod 55 of either medial rod 46 or lateral rod 48 and components of footplate 44. Tibia adjustment 54 allows for proper sizing and fit of device 40 about the lower leg or calf 14 of user 22. Tibia adjustment 54 also facilitates use of device 40 with users of varying leg length.

Furthermore, independent tibia adjustment 54 allows for medial rod 46 and lateral rod 48 to have different heights. As illustrated in FIG. 4, knee hinges 52 for medial rod 46 and lateral rod 48 share the same axis of rotation. However, knee hinges 52 are not required to be coaxial or may be coaxial. Device 40 with non-coaxial knee hinges 52 may be useful for a user having Genu Varum, Genu Valgum, Tibial Varum, or Tibial Valgum deformity. Device 40 with multiaxial ankle hinges 58 may be useful to provide ankle dorsiflexion of user 22 and correction of forefoot varus, forefoot valgus, rearfoot varus, or rearfoot valgus.

Footplate 44 is described as the base of device 40 and support for foot 18 of user 22. Footplate 44 is well padded, including heel 36. Footplate 44 is also adjustable in width from narrow to wide for wider legs or feet 18 of user 22.

Footplate 44 is also adjustable to allow for shoe size-based adjustment from back to front. This shoe size adjustment ranges in various embodiments from children's size 1 pediatric shoes to adult size 24. Adjustment would vary by device 40 depending on the target user group. For example, one common size range adjusts from size 6 female to size 14 male.

Footplate 44 includes ankle hinge 58, sole 60, and optional toe wedge 62. Ankle hinge 58 connects medial rod 46 and lateral rod 48 to footplate 44. Ankle hinge 58 is configured to be located adjacent to the ankle of user 22.

Ankle hinge 58 allows for plantarflexion and dorsiflexion of the ankle of user 22. Ankle hinge 58 allows for precise control of ankle position of user 22. Ankle hinge 58 also includes a locking feature which allows user's ankle to be locked in any position, such as normal, plantarflexion or dorsiflexion. In combination with other components of device 40, ankle hinge 58 aids in stretching user's gastrocnemius and soleus muscles, among other things. Specifically, ankle hinge 58 allows for locking user's ankle in dorsiflexion while knee hinge 52 allows for locking user's knee in extension. The combination of knee in extension and ankle in dorsiflexion aids in full stretching of the gastrocnemius and soleus muscles of user 22.

Footplate 44 also includes goniometer 64 located near ankle hinge 58. Goniometer 64 allows for precise measurement of user's ankle position. It is also envisioned that external locking systems, such as a lockout pin (not shown), may be utilized to hold footplate 44 at a prescribed ankle position. This requested ankle position can be precisely measured, monitored, or adjusted with reference to goniometer 64.

Sole 60 is removably coupled to the bottom side of footplate 44 and includes tread pattern 61 to prevent slippage. As shown in FIG. 4, sole 60 is illustrated as a negative heel rocker sole. Negative heel rocker sole 60 is useful for walking or standing with fixed dorsiflexion ankle joint position. Multiple negative heel rocker soles 60 are available at varying angles to match different angles of dorsiflexion. For example, negative heel rocker sole 60 may have five-degree (5°), ten-degree (10°), and fifteen-degree (15°) angles. Additional negative heel rocker sole degree angles are envisioned.

Toe wedge 62 is optionally included with footplate 44. Toe wedge 62 is configured to be located beneath the hallux of user 22. Toe wedge 62 is configured to engage user's Windlass Mechanism, which dorsiflexes the hallux to tighten the plantar fascia thereby supinating the hindfoot and further stretching the Gastrocsoleus complex and additionally the plantar fascia. Multiple toe wedges 62 are available at varying angles. For example, toe wedges 62 may have any degree from thirty degree (30°) to ninety degree) (90°) angles. Additional toe wedge angles are envisioned. Alternative mechanisms for engaging the Windlass Mechanism are envisioned. For example, a loop of soft rubber may go over the hallux to dorsiflex the ankle of user 22 in order to engage the Windlass Mechanism with a Velcro strap.

Device 40 may also include adjustable straps 66 with optional padding 68 over the thigh, over the lower leg or calf 14, the dorsal midfoot and at ankle 16. Adjustable straps 66 and padding 68 extend about 4-6 cm anterior and posterior above knee 12 of user 22. Additional adjustable straps 66 with pads 68 anterior and posterior to the tibia and calf extending from the tibial tubercle to the inferior border of the calf of user 22 are also envisioned.

Figure 5:
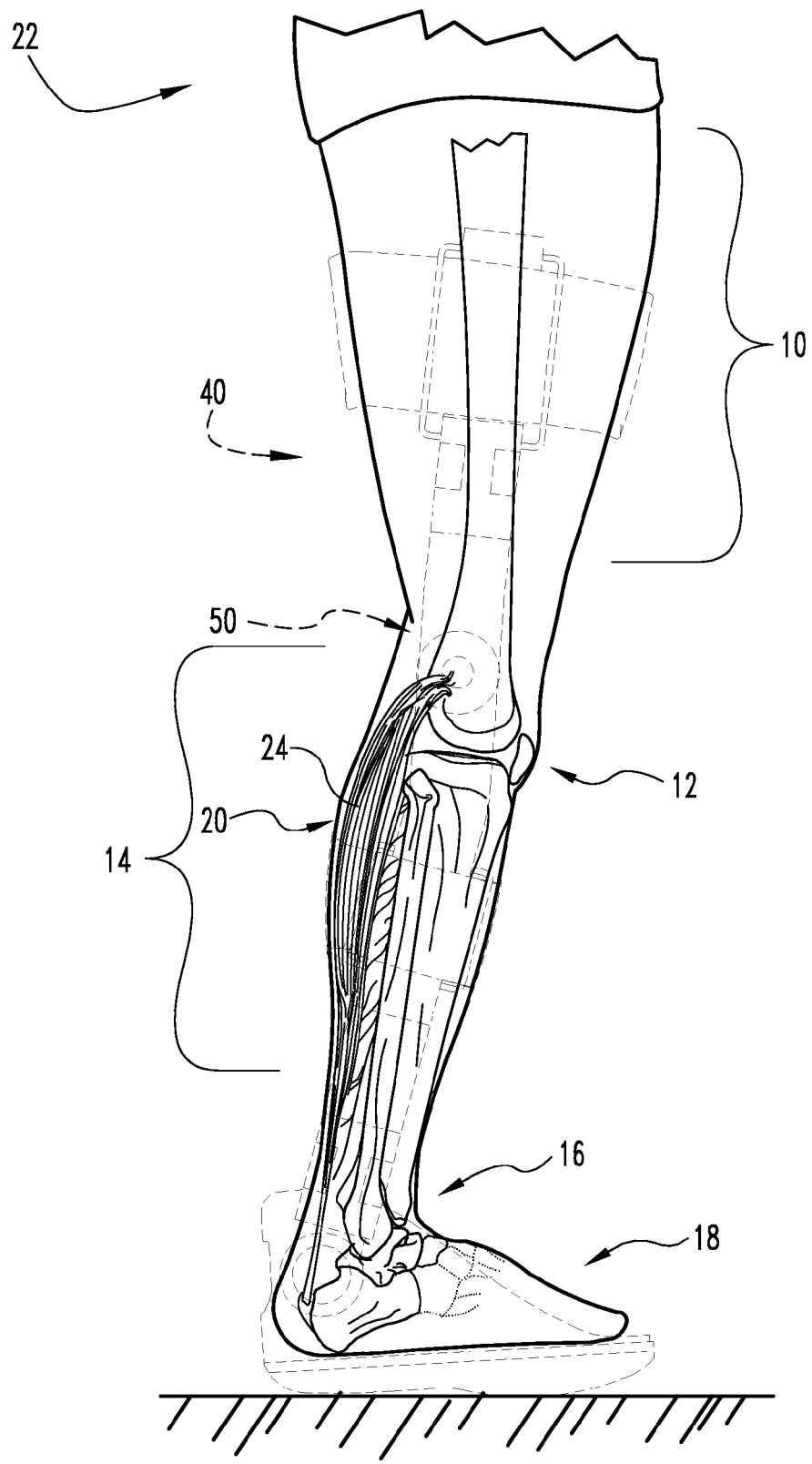
FIG. 5 is a side view of the brace of FIG. 4 and calf muscles with a knee at extension and an ankle in dorsiflexion.

FIG. 5 illustrates device 40 in use by user 22. Device 40 is effective in treating equinus. Device 40 is also effective in treating equinus associated with any of the following other conditions: Heel Spur Syndrome/Plantar fasciitis; neuromuscular disorders such as Cerebral Palsy and Friedreich's Ataxia; congenital disorders such as Congenital Equinus, Clubfoot, Vertical Talus, and, Calcaneal Valgus; Pediatric Flexible Flatfoot deformity; Adult Flexible Flatfoot deformity; Tibialis Posterior Tendon Dysfunction; Achilles tendonitis; Achilles tendon injuries; Haglund's Deformity; Retrocalcaneal heel spurs and tendonosis; Tarsal Coalitions; Bunion deformities; Metatarsalgia; Forefoot pain; Charcot deformity; Diabetic forefoot ulcers and toe ulcers; Equinovarus deformities from post-injury or post-stroke patients; Post Transmetatarsal or Chopart's amputation patients; Midfoot degenerative joint disease at Lis Franc's joint or Chopart's joint; Hypermobile first ray disorders and Cross-over toe deformities.

FIG. 5 is also useful in illustrating methods of treating equinus by stretching user's gastrocnemius muscle. The following illustrated steps of treating equinus using device 40 are: (a) locking knee 12 of user 22 in extension using knee hinge 52 of device 40, (b) locking ankle 16 of user 22 in dorsiflexion using ankle hinge 58 of device 40, thereby stretching user's gastrocnemius muscle 24 and soleus muscle 26. In another embodiment, the additional step of measuring the angle of user's ankle 16 is evident by use of goniometer 64 (FIG. 4) of device 40.

Because device 40 is a targeted stretch of gastrocnemius muscle 24 and soleus muscle 26, device 40 may be used for a shorter period of time than a traditional night splint. Device 40 may yield quicker and more effective results in correction of equinus. Device 40 may provide the same benefit of a traditional night splint without user 22 having to wear device 40 overnight. For example, device 40 worn for two 30 minute sessions per day may provide the same benefit of a traditional night splint worn overnight. This example is based on a meta-analysis by Radford et al. in the British Journal of Sports Medicine 2006. In comparison to a traditional night splint, device 40 may not need to be worn overnight, improving user compliance and providing user with a more comfortable and restful sleep.

Device 40 may be used for a shorter treatment period than other devices. For example, device 40 may be used for one (1) to three (3) months. Some users, especially athletic participants and children, may benefit from a maintenance program after treatment. The maintenance program may involve use of device 40 on a less regular schedule for a period of time to maintain the desired correction.

Device 40 may come with written or digital instructions for users, physicians and therapists. Device 40 may be packaged with Frequently Asked Questions or links to websites for additional information, such as instructions on use.

While the inventions have been illustrated and described in detail in the drawings and foregoing description, the same is to be considered as illustrative and not restrictive in character, it being understood that the preferred embodiment has been shown and described and that changes and modifications that come within the spirit of the invention are desired to be protected.

What is claimed is:

1. A device for treating ankle equinus by stretching the Gastrocnemius muscle and soleus muscle, the brace comprising:
   elongated rods which extend from above the knee of the user to the foot of the user, the rods including a medial elongated rod along a medial side of the leg of the user, the rods including a lateral elongated rod along a lateral side of the leg of the user,
   each rod including a locking knee hinge, the locking knee hinge located somewhat at, below or above the knee, the locking knee hinge locking the knee in an extended position at times, the locking knee hinge releasing the knee to a bent position at other times,
   each rod including adjustable bars to extend proximally toward the user, the adjustable bars being adjustable to change the overall length of the device to accommodate different leg lengths of different users, and
   locking ankle hinges coupling the elongated rods to a footplate, each ankle hinge locking the ankle in a dorsiflexion position at times, each ankle hinge locking the ankle in a normal position or a plantarflexion position at other times;
   wherein the locking knee hinges are coaxial or non-coaxial.

2. The device of claim 1, wherein the locking knee hinge is located somewhat at, below or above the knee to allow for an upper portion of the elongated rod to move ventral along a sagittal plane of the user.

3. The device of claim 2, wherein the locking knee hinge rotates the upper portion of the elongated rod ventral along a sagittal plane of the user to provide easier insertion of the foot and leg of the user.

4. The device of claim 3, wherein the locking knee hinge rotates the upper portion of the elongated rod forward to increase extension of the knee of the user.

5. The device of claim 1 further comprising a wedge supported by the footplate.

6. The device of claim 5, wherein the wedge is located beneath the hallux of the user.

7. The device of claim 5, wherein the wedge is configured to engage the user's Windlass Mechanism.

8. The device of claim 1, wherein the footplate includes a negative heel rocker sole.

9. The device of claim 8 the negative heel rocker sole having a degree angle to match an angle of dorsiflexion of the ankle when the ankle hinge locks the ankle in a dorsiflexion position.

10. The device of claim 9 the negative heel rocker sole having a degree angle selected from the group consisting of 5, 10, and 15 degrees.

11. The device of claim 1, wherein the ankle hinges each include a goniometer which measures the angle between each elongated rod and the footplate.

12. A brace for treating ankle equinus by stretching the Gastrocnemius muscle and soleus muscle, the brace comprising:
   elongated rods which extend from above the knee of the user to the foot of the user, the rods including a medial elongated rod along a medial side of the leg of the user, the rods including a lateral elongated rod along a lateral side of the leg of the user,
   each rod including a locking knee hinge, the locking knee hinge located somewhat below the knee, the locking knee hinge locking the knee in an extended position at times, the locking knee hinge releasing the knee to a bent position at other times,
   an elongated rod along each side of the leg of the user, the locking knee hinges positioned coaxial or non-coaxial relative to each other, each of the hinges near the knee of the user, the hinges locking the knee of the user in an extended position at times, the hinges releasing the knee to a bent position at other times,
   each rod including adjustable bars to extend each rod proximally toward the user, the adjustable bars being adjustable to change the overall length of the device to accommodate different leg lengths of different users, and
   locking ankle hinges coupling the elongated rods to a footplate, each ankle hinge locking the ankle in a dorsiflexion position at some times, each ankle hinge locking the ankle in a normal position or a plantarflexion position at other times;
   wherein the non-coaxial locking knee hinges allow for ankle dorsiflexion of the user, the user having any condition selected from the group consisting of: Genu Varum, Genu Valqum, Tibial Varum, and Tibial Valqum deformity.

13. The device of claim 12, wherein the non-coaxial locking ankle hinges providing ankle dorsiflexion of the user and correction of forefoot varus, forefoot valgus, rearfoot varus, or rearfoot valgus.

14. The device of claim 12, wherein the ankle hinges each include a goniometer which measures the angle between each elongated rod and the footplate.

15. A method of treating equinus by stretching the Gastrocnemius muscle, the method comprising the steps of:
   locking the knee of the user in extension by using a locking knee hinge of a brace having an above-the-knee extension and
   dorsiflexion of the foot of the user at the ankle joint of the user by using a locking ankle hinge of the brace.

16. The method of claim 15, wherein the brace has a goniometer, and further comprising the step of measuring the angle of the ankle of the user using the brace.

17. The method of claim 15, wherein the equinus is associated with any condition selected from the group consisting of:
   a. Heel Spur Syndrome, Plantar fasciitis
   b. Neuromuscular disorders including disorders selected from the group consisting of Cerebral Palsy and Friedreich's Ataxia
   c. Congenital disorders including disorders selected from the group consisting of Congenital equinus, Clubfoot, Vertical Talus and Calcaneal Valgus
   d. Pediatric Flexible Flatfoot deformity
   e. Adult Flexible Flatfoot deformity
   f. Tibialis Posterior Tendon Dysfunction
   g. Achilles tendonitis
   h. Achilles tendon injuries
   i. Haglund's Deformity
   j. Retrocalcaneal heel spurs and tendonosis
   k. Tarsal Coalitions
   l. Bunion deformities
   m. Metatarsalgia
   n. Forefoot pain
   o. Charcot deformity
   p. Diabetic forefoot ulcers and toe ulcers
   q. Equinovarus deformities from post-injury or post-stroke patients
   r. Post Transmetatarsal or Chopart's amputation patients
   s. Midfoot degenerative joint disease at Lis Franc's joint or Chopart's joint
   t. Hypermobile first ray disorders and
   u. Cross-over toe deformities.

18. A device for treating ankle equinus by stretching the Gastrocnemius muscle and soleus muscle, the brace comprising:
   elongated rods which extend from above the knee of the user to the foot of the user, the rods including a medial elongated rod along a medial side of the leg of the user, the rods including a lateral elongated rod along a lateral side of the leg of the user,
   each rod including a locking knee hinge, the locking knee hinge located somewhat at, below or above the knee, the locking knee hinge locking the knee in an extended position at times, the locking knee hinge releasing the knee to a bent position at other times,
   each rod including adjustable bars to extend proximally toward the user, the adjustable bars being adjustable to change the overall length of the device to accommodate different leg lengths of different users, and
   locking ankle hinges coupling the elongated rods to a footplate, each ankle hinge locking the ankle in a dorsiflexion position at times, each ankle hinge locking the ankle in a normal position or a plantarflexion position at other times;
   wherein the ankle hinges each include a goniometer which measures the angle between each elongated rod and the footplate.

19. The device of claim 18, wherein the locking knee hinge is located somewhat at, below or above the knee to allow for an upper portion of the elongated rod to move ventral along a sagittal plane of the user.

20. The device of claim 19, wherein the locking knee hinge rotates the upper portion of the elongated rod ventral along a sagittal plane of the user to provide easier insertion of the foot and leg of the user.

21. The device of claim 20, wherein the locking knee hinge rotates the upper portion of the elongated rod forward to increase extension of the knee of the user.

22. The device of claim 18, wherein the locking knee hinges are coaxial or non-coaxial.

23. The device of claim 18 further comprising a wedge supported by the footplate.

24. The device of claim 23, wherein the wedge is located beneath the hallux of the user.

25. The device of claim 23, wherein the wedge is configured to engage the user's Windlass Mechanism.

26. The device of claim 18, wherein the footplate includes a negative heel rocker sole.

27. The device of claim 26 the negative heel rocker sole having a degree angle to match an angle of dorsiflexion of the ankle when the ankle hinge locks the ankle in a dorsiflexion position.

28. The device of claim 27 the negative heel rocker sole having a degree angle selected from the group consisting of 5, 10, and 15 degrees.

29. A brace for treating ankle equinus by stretching the Gastrocnemius muscle and soleus muscle, the brace comprising:
   elongated rods which extend from above the knee of the user to the foot of the user, the rods including a medial elongated rod along a medial side of the leg of the user, the rods including a lateral elongated rod along a lateral side of the leg of the user,
   each rod including a locking knee hinge, the locking knee hinge located somewhat below the knee, the locking knee hinge locking the knee in an extended position at times, the locking knee hinge releasing the knee to a bent position at other times,
   an elongated rod along each side of the leg of the user, the locking knee hinges positioned coaxial or non-coaxial relative to each other, each of the hinges near the knee of the user, the hinges locking the knee of the user in an extended position at times, the hinges releasing the knee to a bent position at other times,
   each rod including adjustable bars to extend each rod proximally toward the user, the adjustable bars being adjustable to change the overall length of the device to accommodate different leg lengths of different users, and
   locking ankle hinges coupling the elongated rods to a footplate, each ankle hinge locking the ankle in a dorsiflexion position at some times, each ankle hinge locking the ankle in a normal position or a plantarflexion position at other times;

wherein the non-coaxial locking ankle hinges providing ankle dorsiflexion of the user and correction of forefoot varus, forefoot valgus, rearfoot varus, or rearfoot valgus.

30. The device of claim 29, wherein the non-coaxial locking knee hinges allow for ankle dorsiflexion of the user, the user having any condition selected from the group consisting of: Genu Varum, Genu Valgum, Tibial Varum, and Tibial Valgum deformity.

31. The device of claim 29, wherein the ankle hinges each include a goniometer which measures the angle between each elongated rod and the footplate.

32. A brace for treating ankle equinus by stretching the Gastrocnemius muscle and soleus muscle, the brace comprising:
- elongated rods which extend from above the knee of the user to the foot of the user, the rods including a medial elongated rod along a medial side of the leg of the user, the rods including a lateral elongated rod along a lateral side of the leg of the user,
- each rod including a locking knee hinge, the locking knee hinge located somewhat below the knee, the locking knee hinge locking the knee in an extended position at times, the locking knee hinge releasing the knee to a bent position at other times,
- an elongated rod along each side of the leg of the user, the locking knee hinges positioned coaxial or non-coaxial relative to each other, each of the hinges near the knee of the user, the hinges locking the knee of the user in an extended position at times, the hinges releasing the knee to a bent position at other times,
- each rod including adjustable bars to extend each rod proximally toward the user, the adjustable bars being adjustable to change the overall length of the device to accommodate different leg lengths of different users, and
- locking ankle hinges coupling the elongated rods to a footplate, each ankle hinge locking the ankle in a dorsiflexion position at some times, each ankle hinge locking the ankle in a normal position or a plantarflexion position at other times;
- wherein the ankle hinges each include a goniometer which measures the angle between each elongated rod and the footplate.

33. The device of claim 32, wherein the non-coaxial locking knee hinges allow for ankle dorsiflexion of the user, the user having any condition selected from the group consisting of: Genu Varum, Genu Valgum, Tibial Varum, and Tibial Valgum deformity.

34. The device of claim 32, wherein the non-coaxial locking ankle hinges providing ankle dorsiflexion of the user and correction of forefoot varus, forefoot valgus, rearfoot varus, or rearfoot valgus.

* * * * *